United States Patent
Singh et al.

(10) Patent No.: US 11,602,375 B2
(45) Date of Patent: Mar. 14, 2023

(54) METHODS AND DEVICES FOR PROTECTING CATHETER TIPS AND STEREOTACTIC FIXTURES FOR MICROCATHETERS

(71) Applicant: ALCYONE THERAPEUTICS, INC., Lowell, MA (US)

(72) Inventors: Deep Arjun Singh, Cambridge, MA (US); P J Anand, Lowell, MA (US)

(73) Assignee: ALCYONE THERAPEUTICS, INC., Lowell, MA (US)

( * ) Notice: Subject to any disclaimer, the term of this patent is extended or adjusted under 35 U.S.C. 154(b) by 744 days.

(21) Appl. No.: 16/590,336

(22) Filed: Oct. 1, 2019

(65) Prior Publication Data

US 2020/0101239 A1 Apr. 2, 2020

Related U.S. Application Data

(63) Continuation of application No. 14/306,925, filed on Jun. 17, 2014, now Pat. No. 10,456,533.

(60) Provisional application No. 61/984,061, filed on Apr. 25, 2014, provisional application No. 61/835,905, filed on Jun. 17, 2013.

(51) Int. Cl.
*A61B 90/11* (2016.01)
*A61B 17/34* (2006.01)
*A61M 5/46* (2006.01)
*A61B 90/00* (2016.01)

(52) U.S. Cl.
CPC .......... *A61B 17/3496* (2013.01); *A61B 90/11* (2016.02); *A61B 2090/034* (2016.02); *A61M 5/46* (2013.01)

(58) Field of Classification Search
CPC ..... A61B 90/10; A61B 90/11; A61B 17/3496; A62B 2090/034
See application file for complete search history.

(56) References Cited

U.S. PATENT DOCUMENTS

| 2,830,587 A | 4/1958 | Everett |
| 3,460,537 A | 8/1969 | Zeis |
| 3,886,948 A | 6/1975 | Hakim |
| 4,146,029 A | 3/1979 | Ellinwood, Jr. |
| 4,692,146 A | 9/1987 | Hilger |
| 4,885,945 A | 12/1989 | Chiodo |

(Continued)

FOREIGN PATENT DOCUMENTS

| CN | 101123919 A | 2/2008 |
| CN | 101657189 A | 2/2010 |

(Continued)

OTHER PUBLICATIONS

Burmeister et al.; Improved Ceramic-Based Multisite Microelectrode for Rapid Measurements of L-Giutamate in the CNS; Journal of Neuroscience Methods 119 (2002) 163-171; Elsevier Science B.V.

(Continued)

*Primary Examiner* — Katherine H Schwiker

(74) *Attorney, Agent, or Firm* — Marshall, Gerstein & Borun LLP

(57) ABSTRACT

Methods and devices are disclosed herein that generally provide protection for devices (e.g., microcatheters) having small tips. Methods and devices are also disclosed herein that generally facilitate use of commercially-available stereotactic systems with devices (e.g., microcatheters) having small tips.

43 Claims, 11 Drawing Sheets

(56) References Cited

U.S. PATENT DOCUMENTS

| | | |
|---|---|---|
| 4,917,686 A | 4/1990 | Bayston et al. |
| 4,979,284 A | 12/1990 | McMurtry et al. |
| 5,088,208 A | 2/1992 | Wells et al. |
| 5,101,548 A | 4/1992 | McMurtry et al. |
| 5,190,046 A | 3/1993 | Shturman |
| 5,407,431 A | 4/1995 | Botich et al. |
| 5,415,648 A | 5/1995 | Malay et al. |
| 5,509,910 A | 4/1996 | Lunn |
| 5,590,657 A | 1/1997 | Cain et al. |
| 5,620,479 A | 4/1997 | Diederich |
| 5,624,396 A | 4/1997 | McNamara et al. |
| 5,695,518 A | 12/1997 | Laerum |
| 5,720,720 A | 2/1998 | Laske et al. |
| 5,782,645 A | 7/1998 | Stobie et al. |
| 5,843,150 A | 12/1998 | Dreessen et al. |
| 5,868,711 A | 2/1999 | Kramer et al. |
| 5,954,687 A | 9/1999 | Baudino |
| 5,963,367 A | 10/1999 | Aksyuk et al. |
| 6,061,587 A | 5/2000 | Kucharczyk et al. |
| 6,176,842 B1 | 1/2001 | Tachibana et al. |
| 6,193,963 B1 | 2/2001 | Stern et al. |
| 6,200,291 B1 | 3/2001 | Di Pietro |
| 6,224,566 B1 | 5/2001 | Loeb |
| 6,309,634 B1 | 10/2001 | Bankiewicz et al. |
| 6,454,945 B1 | 9/2002 | Weigl et al. |
| 6,464,662 B1 | 10/2002 | Raghavan et al. |
| 6,464,687 B1 | 10/2002 | Ishikawa et al. |
| 6,471,993 B1 | 10/2002 | Shastri et al. |
| 6,547,779 B2 | 4/2003 | Levine et al. |
| 6,599,274 B1 | 7/2003 | Kucharczyk et al. |
| 6,610,235 B1 | 8/2003 | Lebouitz et al. |
| 6,626,902 B1 | 9/2003 | Kucharczyk et al. |
| 6,706,009 B2 | 3/2004 | Diermann et al. |
| 6,803,568 B2 | 10/2004 | Bousse et al. |
| 6,953,575 B2 | 10/2005 | Bankiewicz et al. |
| 7,029,697 B2 | 4/2006 | Segura et al. |
| 7,048,716 B1 | 5/2006 | Kucharczyk et al. |
| 7,316,676 B2 | 1/2008 | Peyman et al. |
| 7,534,613 B2 | 5/2009 | Bankiewicz et al. |
| 7,549,989 B2 | 6/2009 | Morgan et al. |
| 7,588,574 B2 | 9/2009 | Assell et al. |
| 7,690,325 B2 | 4/2010 | Henderson et al. |
| 7,713,269 B2 | 5/2010 | Auge, II et al. |
| 7,771,387 B2 | 8/2010 | Porter |
| 7,842,006 B2 | 11/2010 | Wang et al. |
| 7,984,929 B2 | 7/2011 | Gill |
| 8,128,600 B2 | 3/2012 | Gill |
| 8,192,366 B2 | 6/2012 | Mauge et al. |
| 8,282,566 B2 | 10/2012 | Mauge et al. |
| 8,309,355 B2 | 11/2012 | Bankiewicz et al. |
| 8,347,696 B2 | 1/2013 | Espinosa et al. |
| 8,539,905 B2 | 9/2013 | Cady et al. |
| 8,602,644 B2 | 12/2013 | Choi |
| 8,790,317 B2 | 7/2014 | Olbricht et al. |
| 8,814,853 B2 | 8/2014 | Bosel |
| 8,992,458 B2 | 3/2015 | Singh et al. |
| 9,255,245 B2 | 2/2016 | Bernick et al. |
| 9,445,838 B2 | 9/2016 | Wei et al. |
| 9,844,585 B2 | 12/2017 | Olbricht et al. |
| 9,919,129 B2 | 3/2018 | Singh et al. |
| 10,065,016 B2 | 9/2018 | Singh et al. |
| 10,441,770 B2 | 10/2019 | Singh et al. |
| 10,456,533 B2 | 10/2019 | Singh et al. |
| 2001/0005552 A1 | 6/2001 | Berg et al. |
| 2002/0055702 A1 | 5/2002 | Atala et al. |
| 2002/0055731 A1 | 5/2002 | Atala et al. |
| 2002/0099356 A1 | 7/2002 | Unger et al. |
| 2002/0138036 A1 | 9/2002 | Babaev |
| 2002/0193817 A1 | 12/2002 | Lal et al. |
| 2003/0009153 A1 | 1/2003 | Brisken et al. |
| 2003/0048969 A1 | 3/2003 | Hunter et al. |
| 2003/0093032 A1 | 5/2003 | Py et al. |
| 2003/0138403 A1 | 7/2003 | Drustrup |
| 2003/0148539 A1 | 8/2003 | van Dam et al. |
| 2003/0205947 A1 | 11/2003 | Klee et al. |
| 2003/0216685 A1 | 11/2003 | Porter |
| 2003/0216714 A1 | 11/2003 | Gill |
| 2004/0073114 A1 | 4/2004 | Oliver et al. |
| 2004/0106904 A1 | 6/2004 | Gonnelli et al. |
| 2004/0176732 A1 | 9/2004 | Frazier et al. |
| 2004/0186384 A1 | 9/2004 | Babaev |
| 2004/0220543 A1 | 11/2004 | Heruth et al. |
| 2004/0260241 A1 | 12/2004 | Yamamoto et al. |
| 2005/0035983 A1 | 2/2005 | Cruchon-Dupeyrat et al. |
| 2005/0125007 A1 | 6/2005 | Gill |
| 2005/0137134 A1 | 6/2005 | Gill et al. |
| 2005/0137531 A1 | 6/2005 | Prausnitz et al. |
| 2005/0143790 A1 | 6/2005 | Kipke et al. |
| 2005/0154297 A1 | 7/2005 | Gill |
| 2005/0177117 A1 | 8/2005 | Crocker et al. |
| 2005/0190999 A1 | 9/2005 | Hunter et al. |
| 2005/0236566 A1 | 10/2005 | Liu |
| 2005/0269251 A1 | 12/2005 | Cork et al. |
| 2005/0277862 A1 | 12/2005 | Anand |
| 2006/0003310 A1 | 1/2006 | Klauke et al. |
| 2006/0025752 A1 | 2/2006 | Broaddus et al. |
| 2006/0122677 A1 | 6/2006 | Vardiman |
| 2006/0135945 A1 | 6/2006 | Bankiewicz et al. |
| 2006/0211944 A1 | 9/2006 | Mauge et al. |
| 2006/0211945 A1 | 9/2006 | Mauge et al. |
| 2006/0211946 A1 | 9/2006 | Mauge et al. |
| 2007/0005017 A1 | 1/2007 | Alchas et al. |
| 2007/0016041 A1 | 1/2007 | Nita |
| 2007/0055180 A1 | 3/2007 | Deem et al. |
| 2007/0088295 A1 | 4/2007 | Bankiewicz |
| 2007/0093778 A1 | 4/2007 | Cindrich et al. |
| 2007/0123843 A1 | 5/2007 | Gill |
| 2007/0128083 A1 | 6/2007 | Yantz et al. |
| 2007/0163137 A1 | 7/2007 | Hunter et al. |
| 2007/0191767 A1 | 8/2007 | Hennessy et al. |
| 2007/0250054 A1 | 10/2007 | Drake |
| 2007/0276340 A1 | 11/2007 | Poston et al. |
| 2008/0004572 A1 | 1/2008 | Morris et al. |
| 2008/0091104 A1 | 4/2008 | Abraham |
| 2008/0275466 A1 | 11/2008 | Skakoon |
| 2008/0294096 A1 | 11/2008 | Uber, III et al. |
| 2008/0302960 A1 | 12/2008 | Meister et al. |
| 2009/0030373 A1 | 1/2009 | Gill |
| 2009/0048508 A1 | 2/2009 | Gill et al. |
| 2009/0071833 A1 | 3/2009 | Gorfinkel et al. |
| 2009/0088730 A1 | 4/2009 | Hoofnagle et al. |
| 2009/0112278 A1 | 4/2009 | Wingeier et al. |
| 2009/0124976 A1 | 5/2009 | Mittermeyer |
| 2009/0143659 A1 | 6/2009 | Li et al. |
| 2009/0143764 A1 | 6/2009 | Nelson |
| 2009/0198218 A1 | 8/2009 | Gill et al. |
| 2009/0224529 A1 | 9/2009 | Gill |
| 2009/0279815 A1 | 11/2009 | Hunter et al. |
| 2009/0304314 A1 | 12/2009 | Derrick et al. |
| 2010/0030102 A1 | 2/2010 | Poston et al. |
| 2010/0030148 A1 | 2/2010 | Alchas et al. |
| 2010/0042070 A1 | 2/2010 | Gill et al. |
| 2010/0042098 A1 | 2/2010 | Cross et al. |
| 2010/0098767 A1 | 4/2010 | Olbricht et al. |
| 2010/0121307 A1 | 5/2010 | Lockard et al. |
| 2010/0130884 A1 | 5/2010 | Linninger |
| 2010/0145304 A1 | 6/2010 | Cressman |
| 2010/0168583 A1 | 7/2010 | Dausch et al. |
| 2010/0185179 A1 | 7/2010 | Chan |
| 2010/0199788 A1 | 8/2010 | Ayliffe et al. |
| 2010/0217196 A1 | 8/2010 | Nelson |
| 2010/0217228 A1 | 8/2010 | Grahn et al. |
| 2010/0256549 A1 | 10/2010 | Kralick et al. |
| 2010/0298163 A1 | 11/2010 | Juncker et al. |
| 2010/0312193 A1 | 12/2010 | Stratton et al. |
| 2010/0318061 A1 | 12/2010 | Derrick et al. |
| 2010/0318064 A1 | 12/2010 | Derrick et al. |
| 2010/0324127 A1 | 12/2010 | Kay |
| 2011/0003330 A1 | 1/2011 | Durack |
| 2011/0009879 A1 | 1/2011 | Derrick et al. |
| 2011/0098580 A1 | 4/2011 | Mikhail et al. |
| 2011/0106054 A1 | 5/2011 | Osborne et al. |
| 2011/0137289 A1 | 6/2011 | Kunst |
| 2011/0178505 A1 | 7/2011 | Odland et al. |

(56) References Cited

U.S. PATENT DOCUMENTS

| | | |
|---|---|---|
| 2011/0184503 A1 | 7/2011 | Xu et al. |
| 2011/0200244 A1 | 8/2011 | Ashton et al. |
| 2011/0218494 A1 | 9/2011 | Gerrans et al. |
| 2011/0275994 A1 | 11/2011 | Iwase et al. |
| 2011/0282319 A1 | 11/2011 | Gill |
| 2011/0301235 A1 | 12/2011 | Erlanson et al. |
| 2012/0019270 A1 | 1/2012 | Amodei et al. |
| 2012/0041394 A1 | 2/2012 | Haider et al. |
| 2012/0046666 A1 | 2/2012 | Klein |
| 2012/0060847 A1 | 3/2012 | Stratton et al. |
| 2012/0065496 A1 | 3/2012 | Stratton et al. |
| 2012/0083739 A1 | 4/2012 | Nelson |
| 2012/0083742 A1 | 4/2012 | Nelson |
| 2012/0123391 A1 | 5/2012 | Gill et al. |
| 2012/0209110 A1 | 8/2012 | Bankiewicz et al. |
| 2012/0209303 A1 | 8/2012 | Frankhouser et al. |
| 2012/0257846 A1 | 10/2012 | Derrick et al. |
| 2012/0302959 A1 | 11/2012 | Fielder et al. |
| 2012/0310046 A1 | 12/2012 | Stout et al. |
| 2012/0310182 A1 | 12/2012 | Fielder et al. |
| 2012/0310215 A1 | 12/2012 | Stout et al. |
| 2013/0019488 A1 | 1/2013 | McMurtry et al. |
| 2013/0035560 A1 | 2/2013 | Anand et al. |
| 2013/0035574 A1 | 2/2013 | Anand |
| 2013/0035660 A1 | 2/2013 | Anand |
| 2013/0046230 A1 | 2/2013 | Lewis, Jr. et al. |
| 2013/0072882 A1 | 3/2013 | Ogawa et al. |
| 2013/0079596 A1 | 3/2013 | Smith |
| 2013/0079779 A1 | 3/2013 | Smith |
| 2013/0204202 A1 | 8/2013 | Trombly et al. |
| 2013/0310767 A1 | 11/2013 | Solar et al. |
| 2014/0039459 A1 | 2/2014 | Folk et al. |
| 2014/0171760 A1 | 6/2014 | Singh et al. |
| 2014/0171902 A1 | 6/2014 | Singh et al. |
| 2014/0276417 A1 | 9/2014 | Nelson |
| 2014/0371711 A1 | 12/2014 | Singh et al. |
| 2014/0371712 A1 | 12/2014 | Olbricht et al. |
| 2015/0038949 A1 | 2/2015 | Singh et al. |
| 2015/0133887 A1 | 5/2015 | Singh et al. |
| 2016/0213312 A1 | 7/2016 | Singh et al. |
| 2016/0346505 A1 | 12/2016 | Gill et al. |
| 2018/0193595 A1 | 7/2018 | Singh et al. |

FOREIGN PATENT DOCUMENTS

| | | |
|---|---|---|
| EP | 2042212 A1 | 4/2009 |
| JP | 2009-507531 A | 2/2009 |
| JP | 2010-501233 A | 1/2010 |
| JP | 2011-212502 A | 10/2011 |
| WO | WO-95/05864 A1 | 3/1995 |
| WO | WO-97/00442 A1 | 1/1997 |
| WO | WO-97/17105 A1 | 5/1997 |
| WO | WO-97/40874 A1 | 11/1997 |
| WO | WO-97/48425 A2 | 12/1997 |
| WO | WO-98/52064 A1 | 11/1998 |
| WO | WO-99/52585 A1 | 10/1999 |
| WO | WO-00/51669 A1 | 9/2000 |
| WO | WO-02/068036 A1 | 9/2002 |
| WO | WO-02/085431 A2 | 10/2002 |
| WO | WO-2004/060465 A2 | 7/2004 |
| WO | WO-2006/015091 A2 | 2/2006 |
| WO | WO-2007/104953 A1 | 9/2007 |
| WO | WO-2007/133545 A2 | 11/2007 |
| WO | WO-2008/100930 A2 | 8/2008 |
| WO | WO-2008/134509 A1 | 11/2008 |
| WO | WO-2010/006293 A2 | 1/2010 |
| WO | WO-2010/081072 A2 | 7/2010 |
| WO | WO-2011/098769 A1 | 8/2011 |
| WO | WO-2011/109735 A2 | 9/2011 |
| WO | WO-2012/145652 A1 | 10/2012 |
| WO | WO-2013/019830 A2 | 2/2013 |
| WO | WO-2014/016591 A1 | 1/2014 |

OTHER PUBLICATIONS

Chinese Office Action for Application No. 201280046268.8, dated May 27, 2015 (45 pages).

Debinski, W., et al., "Convection-enhanced Delivery for the Treatment of Brain Tumors," Expert Rev Neurother. 2009 PCT; 9(10): 1519-1527.

Extended European Search Report for Application No. 12819276.2, dated Mar. 23, 2015 (7 pages).

Extended European Search Report for Application No. 13865917.2, dated Aug. 17, 2016 (6 pages).

Extended European Search Report for Application No. 14814380.3, dated Nov. 11, 2016. (7 pages).

Extended European Search Report for Application No. 14831460.2, dated Mar. 2, 2017 (7 pages).

Fiandaca, M., et al., "Use of Convection-Enhanced Delivery with Liposomal Toxins in Neurooncology," Toxins 2011, 3 4), 369-397.

International Search Report and Written Opinion for Application No. PCT/2014/049031 dated Jan. 30, 2015 (16 pages).

International Search Report and Written Opinion for Application No. PCT/US2012/049100, dated Jan. 29, 2013. (12 pages).

International Search Report and Written Opinion for Application No. PCT/US2013/076084 dated Mar. 11, 2014 (13 Pages).

International Search Report and Written Opinion for International Application No. PCT/US2014/042726, dated Oct. 28, 2014.

International Search Report for International Application No. PCT/US2011/027238, dated Nov. 16, 2011.

Invitation to Pay Additonal Fees for Application No. PCT/US2014/049031, dated Nov. 24, 2014 (2 pages).

Japanese Office Action for Application No. 2015-549618, dated Sep. 5, 2017 (12 pages).

Japanese Office Action for Application No. 2016-531883, dated Jun. 5, 2018 (10 pages).

Lewis et al., Design and characterization of a high-power ultrasound driver with ultralow-output impedance. Rev Sci Instrum. Nov. 2009;80(11):114704.1-114704.8.

Olbricht, William L. et al., Microfluidic Probes in the Treatment of Brain-Related Diseases, Drug News and Perspectives, 2010, 23(8)—7 pages (Oct. 2010).

Rapoport, S.I., "Osmotic opening of the blood-brain barrier: principles, mechanism, and therapeutic applications," Cell. Mol. Neurobiol. 20: 217-30 (2000).

Saltzman et al.; Building Drug Delivery Into Tissue Engineering; Nature Reviews/Drug Discovery; 2002 Macmillan Magazines Ltd.; vol. 1; Mar. 2002; pp. 177-186.

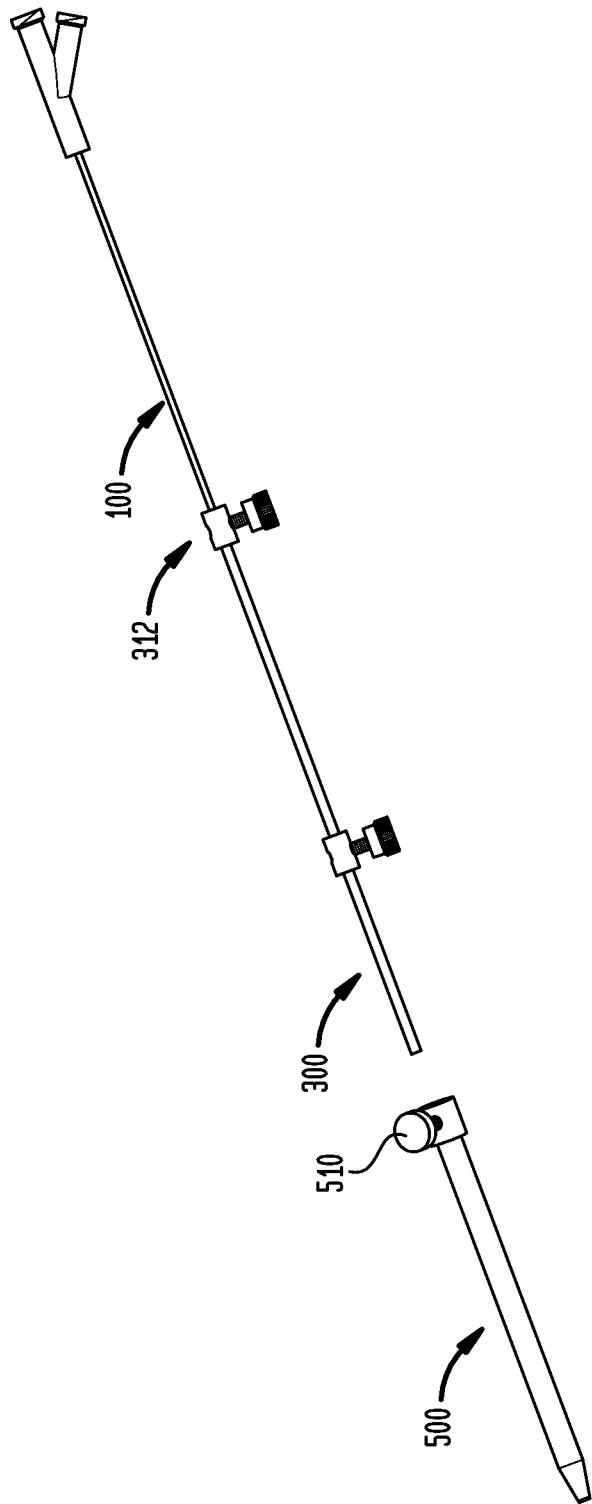
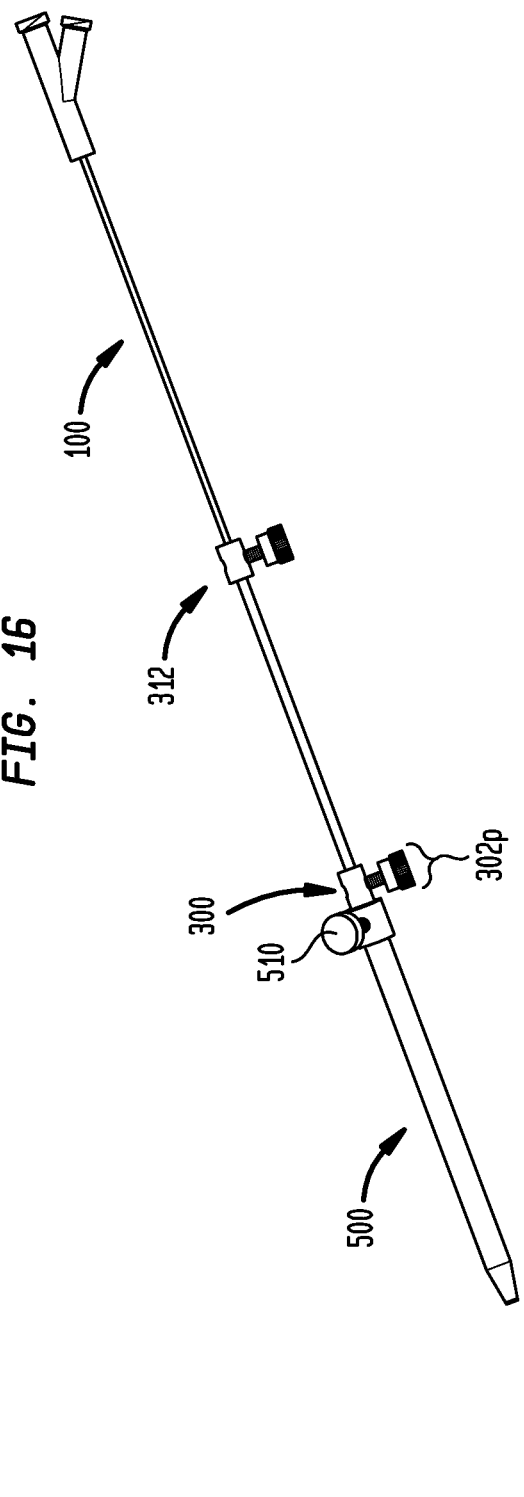

METHODS AND DEVICES FOR PROTECTING CATHETER TIPS AND STEREOTACTIC FIXTURES FOR MICROCATHETERS

CROSS-REFERENCE TO RELATED APPLICATIONS

This application is a continuation of U.S. application Ser. No. 14/306,925 filed on Jun. 17, 2014, which claims priority to U.S. Provisional Application No. 61/835,905 filed on Jun. 17, 2013 and to U.S. Provisional Application No. 61/984,061 filed on Apr. 25, 2014, each of which is hereby incorporated herein by reference in its entirety.

FIELD

Methods and devices for protecting catheter tips and stereotactic fixtures for microcatheters are disclosed herein.

BACKGROUND

In convection-enhanced delivery (CED), drugs are infused locally into tissue through a needle, cannula, or microcatheter inserted into the tissue. Transport of the infused material is dominated by convection, which enhances drug penetration into the target tissue compared with diffusion-mediated delivery or systemic delivery.

The devices used to perform CED, as well as devices used in several other fields, can include a very small, thin tip (e.g., a microfabricated tip). For example, as shown in FIG. 1, a microcatheter 100 can include a catheter body 102 with a microfabricated tip 104 at the distal end thereof. The tip can be damaged or broken during handling and/or during a surgical procedure. For example, the tip can either break during handling as a user hits the catheter tip against an object, or the surgeon may break the tip while inserting it in the brain through a stereotactic system. Stereotactic systems generally have a lumen with a small inside diameter (ID) to snugly fit the catheter. For example, as shown in FIG. 2, an exemplary stereotactic system 200 has a small-diameter central lumen 202 extending therethrough. The surgeon is required to "aim" the small catheter into the tight lumen to get the catheter loaded into the stereotactic system. Catheters with small tips may get damaged as the surgeon may hit the tip against the stereotactic system while manually trying to align the catheter to the small lumen. In addition, stereotactic systems are generally sized for larger instruments and cannot adequately support and protect catheters with small diameters or small tips.

A need exists for methods and devices for protecting catheter tips and stereotactic fixtures for microcatheters.

SUMMARY

Methods and devices are disclosed herein that generally provide protection for devices (e.g., microcatheters) having small tips. Methods and devices are also disclosed herein that generally facilitate use of commercially-available stereotactic systems with devices (e.g., microcatheters) having small tips.

In some embodiments, a tip protection device includes an elongate body having a central lumen extending longitudinally therethrough, the lumen being sized and configured to slidably receive a catheter, and a locking mechanism configured to selectively maintain the elongate body in a fixed longitudinal position relative to a catheter inserted through the central lumen.

The locking mechanism can include a screw. The elongate body can include an increased-diameter portion configured to act as a depth stop when the elongate body is inserted through a lumen of a stereotactic system. The elongate body can be formed from at least one of silastic, poly-urethane, poly-ester, PTFE, E-PTFE, stainless steel, polycarbonate, PVC, Delrin, aluminum, PEEK, plastic, metal, and titanium. The elongate body can be fabricated using at least one of extrusion, molding, and machining. The elongate body can include a sharpened distal tip. The distal tip can be separable from the elongate body along a perforated snap portion. The elongate body can include a distal cylindrical portion having a first diameter and a proximal cylindrical portion having a second diameter that is greater than the first diameter. The central lumen can have a diameter of about 0.5 mm to about 4.0 mm.

In some embodiments, a system includes a tip protection device (e.g., of the type described above) and a depth stop comprising a cylindrical body portion having a central lumen extending longitudinally therethrough and a locking mechanism configured to selectively engage a catheter inserted through the cylindrical body portion.

In some embodiments, a system includes a tip protection device (e.g., of the type described above) and a guide tube that includes an elongate body having a central lumen extending longitudinally therethrough, the central lumen including a proximal portion having a first diameter and a distal portion having a second diameter that is less than the first diameter, the proximal portion being sized to receive a reduced diameter distal portion of the tip protection device and the distal portion being sized to receive at least a portion of a catheter inserted through the tip protection device.

The elongate body of the guide tube can include a proximal portion having an outside diameter which is greater than an outside diameter of a distal portion of the elongate body of the guide tube. A distal end of the guide tube can be tapered. The system can include a guide stop adapter comprising a cylindrical disc having an inside diameter sized to receive the distal portion of the guide tube therethrough and an outside diameter sized to fit within a guide stop of a stereotactic system, and a guide block adapter comprising a cylindrical sleeve having an inside diameter sized to receive the distal portion of the guide tube therethrough and an outside diameter sized to fit within a guide block of a stereotactic system. The guide tube can have a length sufficient to span a distance between the guide block of the stereotactic system and a skull of a patient to which the stereotactic system is registered.

In some embodiments, a method of inserting a catheter into a patient includes registering a stereotactic system to the patient, inserting a catheter having a tip protection device disposed over a distal tip thereof into a working channel of the stereotactic system until a depth stop on the tip protection device prevents further insertion, releasing a locking mechanism of the tip protection device and advancing the catheter distally into the patient, and engaging a locking mechanism of the stereotactic system with the tip protection device, thereby engaging the tip protection device with the catheter to maintain a fixed longitudinal position between the catheter and the stereotactic device.

The method can include delivering a therapeutic agent through the catheter using convection-enhanced delivery. The method can include, before said releasing and engaging, piercing the dura of the patient with a sharpened distal tip of the tip protection device, removing the tip protection device from the stereotactic frame, snapping off the sharpened distal tip of the tip protection device, and reinserting the tip protection device through the stereotactic frame. The method can include inserting the tip protection device through a central lumen of a guide tube mounted in the stereotactic system such that a distal end of the tip protection device is received within a proximal portion of the central lumen of the guide tube. Advancing the catheter can include advancing a distal tip of the catheter through a distal portion of the central lumen of the guide tube, the distal portion of the central lumen of the guide tube having a diameter that is less than a diameter of the proximal portion of the central lumen of the guide tube, such that at least a portion of the catheter is disposed within the distal portion of the central lumen of the guide tube. The method can include inserting the guide tube through a guide stop adapter and a guide block adapter mounted in the stereotactic system.

The present invention further provides devices, systems, and methods as claimed.

BRIEF DESCRIPTION OF THE DRAWINGS

The invention will be more fully understood from the following detailed description taken in conjunction with the accompanying drawings, in which:

FIG. 15 is a perspective view of the tip protector of FIG. 3, the microcatheter of FIG. 1, the depth stop of FIG. 10, and the guide tube of FIG. 13;

FIG. 16 is another perspective view of the tip protector of FIG. 3, the microcatheter of FIG. 1, the depth stop of FIG. 10, and the guide tube of FIG. 13;

DETAILED DESCRIPTION

Methods and devices are disclosed herein that generally provide protection for devices (e.g., microcatheters) having small tips. Methods and devices are also disclosed herein that generally facilitate use of commercially-available stereotactic systems with devices (e.g., microcatheters) having small tips.

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In some embodiments, a tip protector is provided in the form of a sleeve. The sleeve can be formed by cutting a length of tubing or using extrusion, molding, and/or machining processes. The sleeve can include a central lumen extending longitudinally therethrough, defined by a relatively thin wall. The sleeve can be slid over the catheter (or similar small-tip device) to protect the catheter tip from breakage or damage during handling or use. The tip protector can be configured to sit over the catheter or other device such that it covers and protects the micro-tip. The tip protector can be secured on the catheter using a set-screw or a snap feature, or other feature that can easily be undeployed to slide the catheter through the sleeve as needed. The tip protector can be packaged and shipped with the catheter (e.g., with the protector pre-installed over the tip of the catheter).

In use, the surgeon/user can align the catheter to the stereotactic system using the sleeve as a reference. Once aligned, the tip protector and catheter can be slid inside the stereotactic system (the tip protector can be sized to fit existing systems). Once inside the stereotactic system, the user can loosen the set-screw on the tip protector to slide the catheter further into the brain or other tissue. The proximal end of the tip protector can have a large outside diameter (OD) stop or collar that does not allow it to slide inside the stereotactic system as the catheter is being inserted into the brain. Once the catheter is inserted into the brain, the stereotactic system set-screw can be tightened over the tip-protector sleeve (due to the thin wall) onto the catheter to fix it in place and prevent the catheter from sliding. The tip protector can be MRI compatible so that it does not interfere with MR imaging.

Figure 1:
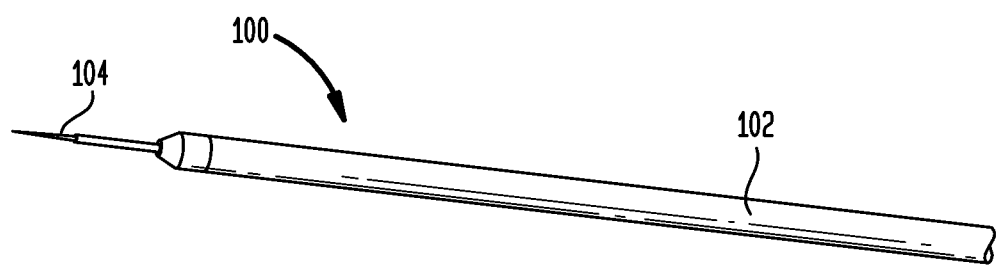
FIG. 1 is a perspective view of an exemplary microcatheter.
Figure 2:
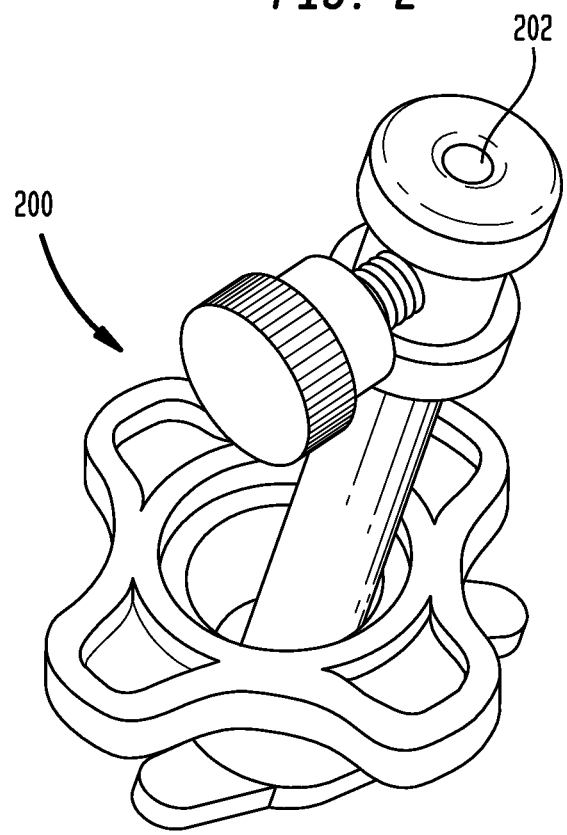
FIG. 2 is a perspective view of an exemplary stereotactic system.
Figure 3:
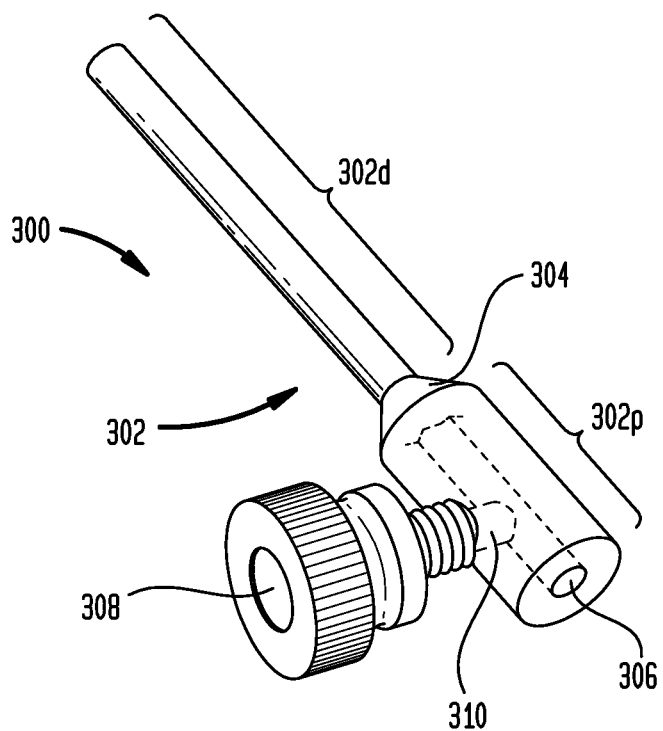
FIG. 3 is a perspective view of an exemplary tip protector.

FIG. 3 illustrates an exemplary embodiment of a tip protector 300 having a set screw and a large diameter stop portion. As shown, the tip protector 300 includes an elongate sleeve 302. The distal portion 320d of the sleeve 302 has an outside diameter which is less than the outside diameter of the proximal portion 302p of the sleeve. The outside diameter of the sleeve 302 can be curved, ramped, stepped, or tapered at the junction of the proximal and distal portions to provide a transition or shoulder 304. This transition 304 can act as a shoulder or stop surface to limit the degree to which the tip protector 300 can be advanced distally through a cylindrical opening, such as the opening of a stereotactic system. A central cylindrical lumen 306 extends through the tip protector 300 from a proximal end of the sleeve 302 to a distal end of the sleeve. The lumen 306 is sized and configured to receive at least a portion of a catheter therethrough. The tip protector 300 also includes a set screw 308 threadably mounted in a channel 310 which extends perpendicular to the central lumen 306. Rotation of the set screw 308 in a first direction can be effective to advance the set screw within the channel 310 such that it extends into the central lumen 306 and engages a catheter or other instrument inserted therethrough. Rotation of the set screw 308 in a second, opposite direction can be effective to withdraw the set screw within the channel 310 such that it does not extend into the central lumen 306 and does not engage a catheter or other instrument inserted therethrough.

Figure 4:
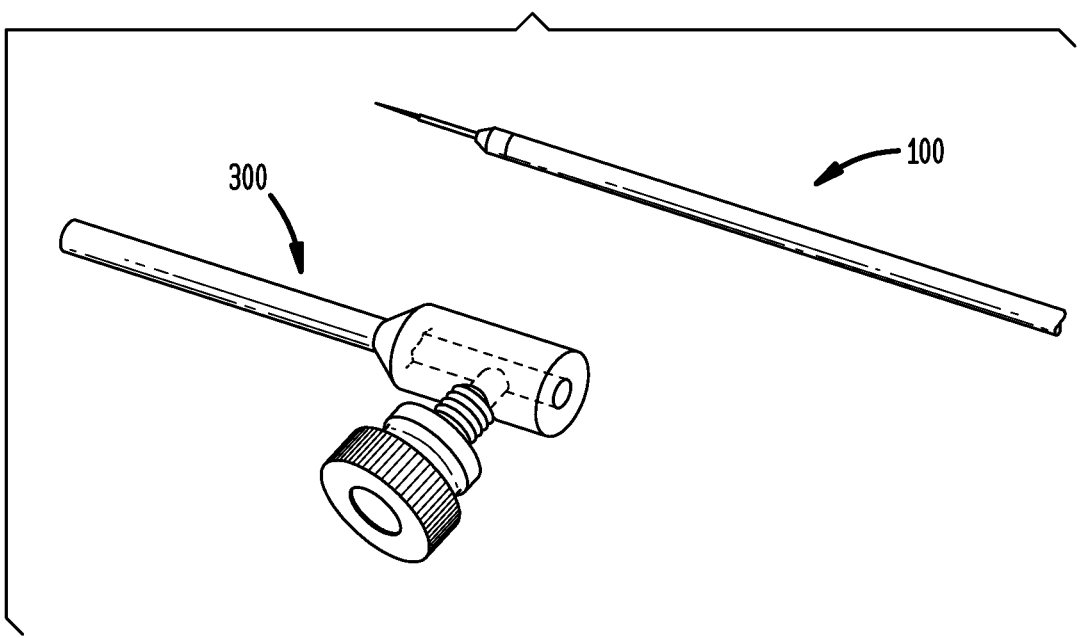
FIG. 4 is a perspective view of the tip protector of FIG. 3 shown with the microcatheter of FIG. 1.

The tip protector 300 is shown in FIG. 4 with an exemplary embodiment of a microcatheter 100 for convection-enhanced delivery. It will be appreciated that any of a variety of microcatheters or other instruments can be used with the tip protector. Exemplary microcatheter devices are disclosed in the following references, the entire contents of each of which are hereby incorporated by reference herein: U.S. Publication No. 2013/0035560 entitled MULTI-DIRECTIONAL MICROFLUIDIC DRUG DELIVERY DEVICE; U.S. Publication No. 2013/0035574 entitled MICROFLUIDIC DRUG DELIVERY DEVICES WITH VENTURI EFFECT; U.S. Publication No. 2013/0035660 entitled MULTIDIRECTIONAL MICROFLUIDIC DRUG DELIVERY DEVICES WITH CONFORMABLE BALLOONS; U.S. application Ser. No. 14/132,762 entitled SYSTEMS AND METHODS FOR REDUCING OR PREVENTING BACKFLOW IN A DELIVERY SYSTEM; U.S. Publication No. 2010/0098767 entitled CONVECTION ENHANCED DELIVERY APPARATUS, METHOD, AND APPLICATION; and U.S. Publication No. 2013/0046230 entitled ULTRASOUND-ASSISTED CONVECTION ENHANCED DELIVERY OF COMPOUNDS IN VIVO WITH A TRANSDUCER CANNULA ASSEMBLY.

Figure 5:
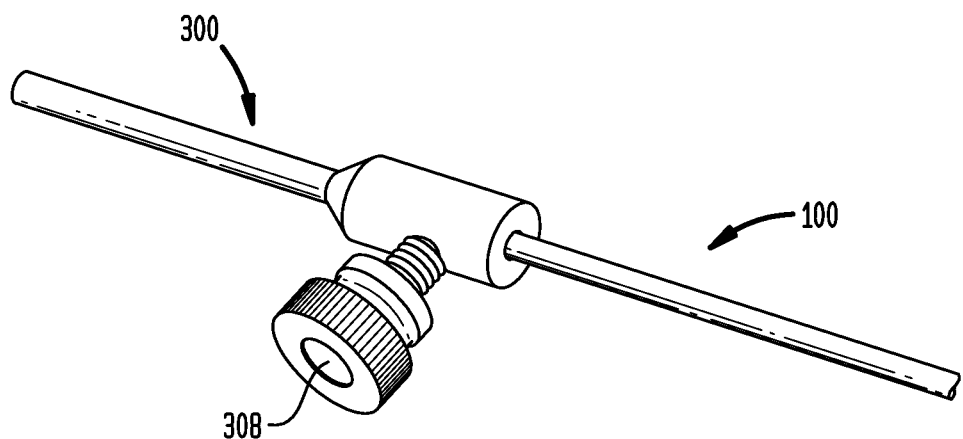
FIG. 5 is another perspective view of the tip protector of FIG. 3 shown with the microcatheter of FIG. 1.
Figure 6:
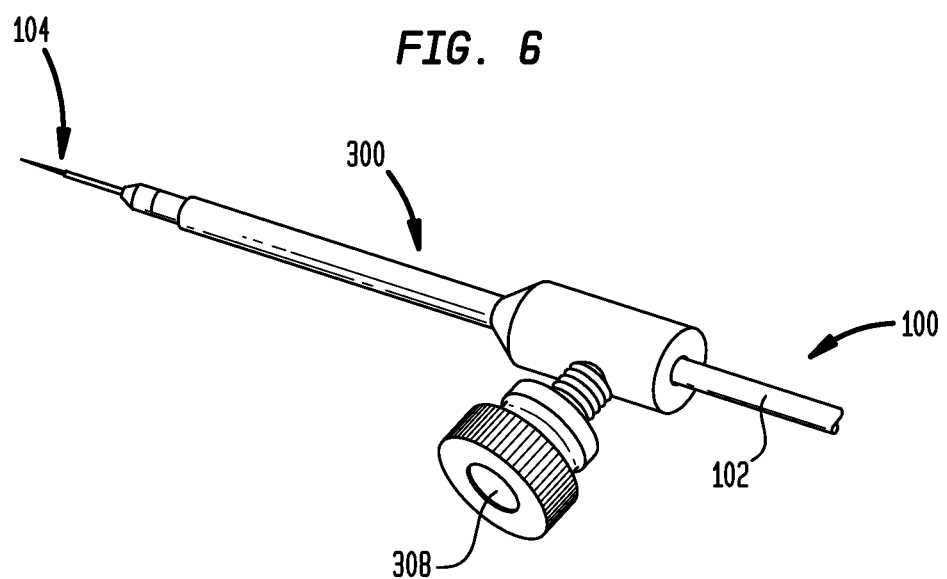
FIG. 6 is another perspective view of the tip protector of FIG. 3 shown with the microcatheter of FIG. 1.

As shown in FIG. 5, the microcatheter 100 can be inserted through the central lumen 306 of the tip protector 300. The set screw 308 can be tightened to secure the tip protector 300 to the microcatheter 100 and prevent longitudinal translation of the tip protector relative to the microcatheter. The microcatheter 100 can also be positioned such that the tip 104 of the microcatheter protrudes from a distal end of the tip protector 300, as shown in FIG. 6. This relative positioning of the tip protector 300 and the microcatheter 100 would typically be used only after the microcatheter is inserted into the stereotactic system, although the user may wish to slide the tip 104 out of the tip protector before insertion to confirm fluid flow during priming, etc., and then retract the tip back into the tip protector before inserting the catheter through the stereotactic system.

Figure 7:
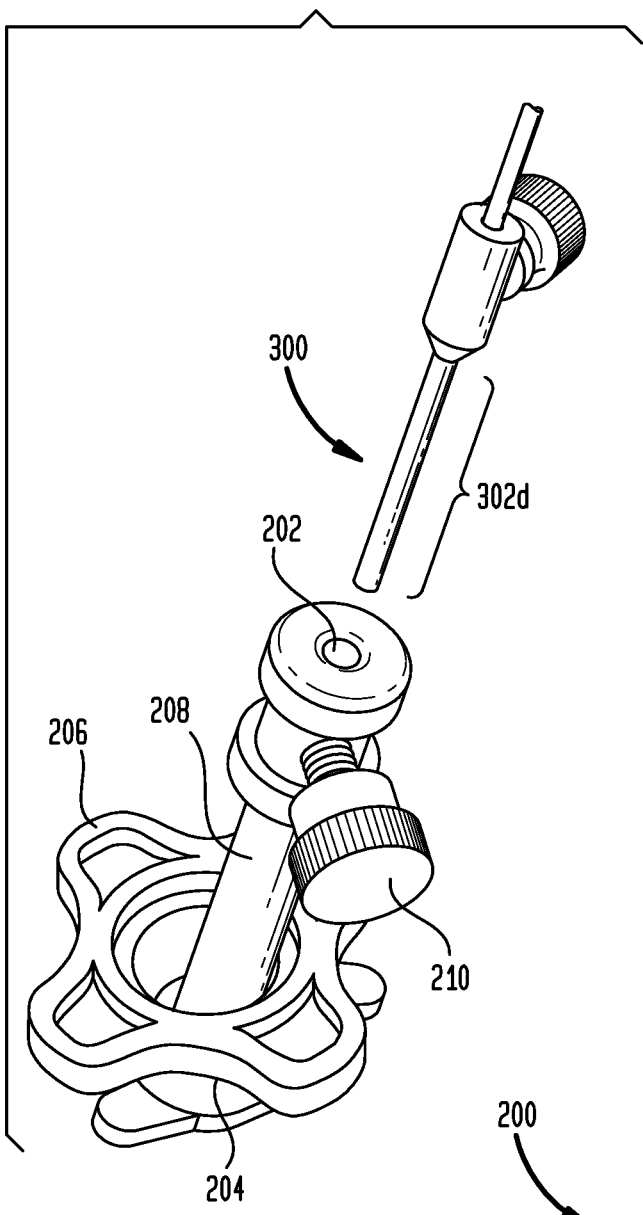
FIG. 7 is a perspective view of the tip protector of FIG. 3, the microcatheter of FIG. 1, and an exemplary stereotactic system.
Figure 8:
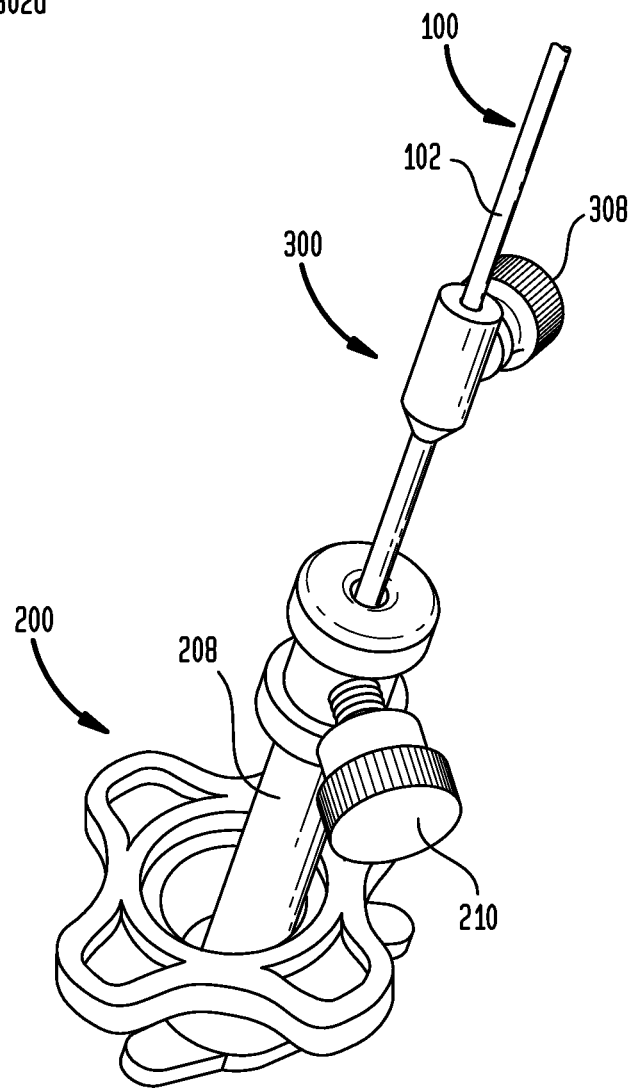
FIG. 8 is another perspective view of the tip protector of FIG. 3, the microcatheter of FIG. 1, and an exemplary stereotactic system.
Figure 9:
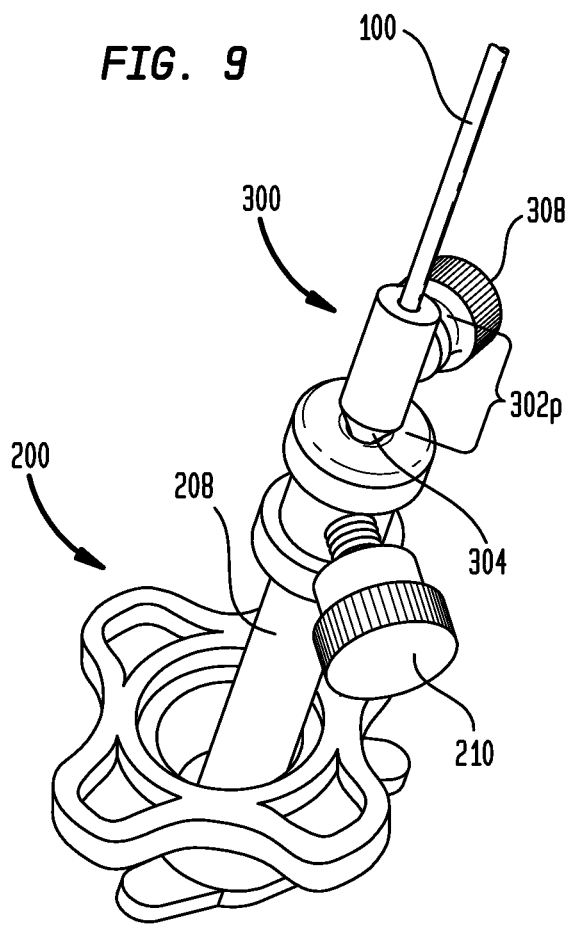
FIG. 9 is another perspective view of the tip protector of FIG. 3, the microcatheter of FIG. 1, and an exemplary stereotactic system.

The tip protector can be used with any of a variety of stereotactic systems. For example, as shown in FIGS. 7-9, the tip protector 300 can be used with a stereotactic system 200 of the type available from MEDTRONIC, INC. under the NAVIGUS brand. The illustrated stereotactic system 200 includes a base 204 with a locking ring 206 and a stem 208 that can be positioned at various angles with respect to the base. The stem 208 includes a set screw 210 to secure a device inserted through an inner lumen 202 of the stem. In use, the base 204 is installed over a portion of the patient (e.g., a burr hole formed in the patient's skull).

As shown in FIG. 7, the microcatheter 100 can be aligned to the small hole 202 in the stem 208 without damaging the catheter tip by using the tip protector 300 as a visual and contact reference. The outside diameter of the distal portion 302d of the tip protector 300 can be sized to substantially match the inside diameter of the central lumen 202 of the stem 208 such that the tip protector fits snugly within the stereotactic system 200, as shown in FIG. 8. As shown in FIG. 9, the tip protector 300 can be advanced distally within the stem 208 until the shoulder portion 304 of the tip protector engages the proximal end of the stem and prevents further insertion. The large diameter stop portion 302p on the tip protector 300 can thus prevent the tip protector from being advanced too far through the stereotactic system 200. The distal portion 302d of the tip protector 300 can have a length that substantially corresponds to the length of the stem 208, such that the distal end of the tip protector is aligned with the distal end of the stereotactic system 200 when the tip protector is inserted up to the shoulder portion 304.

Once the tip protector 300 is inserted through the stem 208, the set screw 308 of the tip protector can be loosened to allow the microcatheter 100 to be translated longitudinally relative to the tip protector and the stem, such that the catheter tip can be advanced distally into the patient or retracted proximally from the patient. The set screw 210 on the stem 208 can be tightened over the tip protector 300 to secure the catheter 100 and the tip protector with respect to the stem.

The terminal distal end of the tip protector 300 can also be made to be sharp and, when the tip protector is fully-advanced into the stereotactic system 200, the distal tip of the tip protector can extend into the skull and past the dura to ensure the dura and corresponding anatomies are pierced and will not interfere with the catheter micro-tip 104 during insertion. For example, the distal tip of the tip protector 300 can be pointed or otherwise sharpened and can extend a few millimeters beyond the skull when inserted through the stereotactic system 200. The length of the tip protector 300 can thus be selected based on the stereotactic system with which it will be used to achieve the desired degree of protrusion. In an exemplary method of use, the catheter 100 and that elongated, sharp-tipped protector 300 can be inserted through the stereotactic system 200 such that the distal tip of the tip protector extends through the skull and a few millimeters past the dura, thereby opening, tearing, and/or piercing the dura. The catheter 100 and the tip protector 300 can then be removed and the sharp tip of the tip protector can be broken or snapped off (e.g., along a perforated snap section or frangible portion) to expose the lumen 306 of the tip protector. The tip protector 300 and the catheter 100 can then be re-inserted and used as described above.

Figure 10:
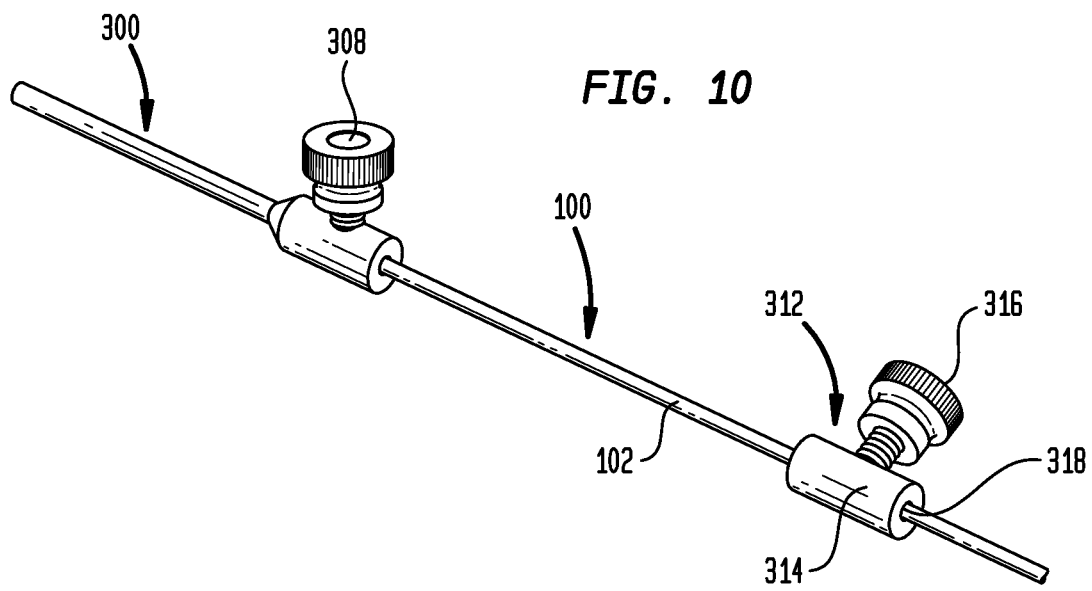
FIG. 10 is a perspective view of the tip protector of FIG. 3, the microcatheter of FIG. 1, and an exemplary depth stop.

As shown in FIG. 10, a depth stop 312 can be included for setting the desired insertion depth of the microcatheter 100 and preventing over-insertion. The illustrated depth stop 312 includes a collar 314 that can be longitudinally slidable with respect to the catheter 100 and can include a thumb screw 316 for engaging the catheter to secure the collar in a fixed longitudinal position with respect thereto. In particular, the set screw 316 can be selectively positioned such that a tip of the set screw extends into a central lumen 318 of the collar 314 to engage the microcatheter 100 disposed therein. As the microcatheter 100 is advanced distally through the tip protector 300, the collar 314 eventually contacts the proximal end of the tip protector, preventing further insertion of the catheter. The depth stop 312 can thus be slid along the catheter 100 and locked in place to set the maximum insertion depth. The catheter 100 can also include depth markings on the catheter body 102 to help a user place the depth stop 312 at the desired calculated depth.

In some embodiments, the tip protector can have a standard length to allow easy depth registration between the tip protector, the catheter, and the stereotactic system. In some embodiments, the distal portion of the tip protector is approximately 5 cm in length and the proximal, increased-diameter portion of the tip protector is approximately 1 cm in length such that the tip protector has an overall length of approximately 6 cm. Accordingly, a catheter with marked depth graduations on its exterior sidewall can be advanced into the tip protector to the 6 cm marking, indicating that the distal end of the catheter is aligned (i.e., not protruding or recessed) with the distal end of the tip protector. Similarly, the tip protector can be fully-advanced into a stereotactic system having a 5 cm stem length, such that the distal end of the tip protector is aligned (i.e., not protruding or recessed) with the distal end of the stereotactic system.

In some embodiments, the central lumen of the tip protector can have an inside diameter that corresponds to (e.g., is substantially equal to or slightly greater than) the outside diameter of the catheter. For example, the central lumen of the tip protector can have a diameter of about 0.5 mm to about 4.0 mm. In some embodiments, the central lumen of the tip protector can have a diameter of about 1.5 mm. In some embodiments, the central lumen of the tip protector can have a diameter of about 3.0 mm.

While an exemplary microcatheter 100 and an exemplary stereotactic system 200 are shown and described above, it will be appreciated that the tip protector 300 can be sized or otherwise configured to work with any of a variety of catheters or other small-tipped devices, and can likewise be sized or otherwise configured to work with any of a variety of stereotactic systems, stems, collets, sleeves, frames, etc. In addition, one or more fixtures, adapters, guides, or other accessories can be included to facilitate use of the tip protector and/or a microcatheter with a particular stereotactic system.

Exemplary stereotactic systems include the NAVIGUS system available from MEDTRONIC, INC. and the VARIOGUIDE system available from BRAINLAB. Both of these systems are "frameless," meaning they are mounted directly or close to the patient's head, and do not need the functional "frame" per conventional stereotactic procedures.

Figure 11:
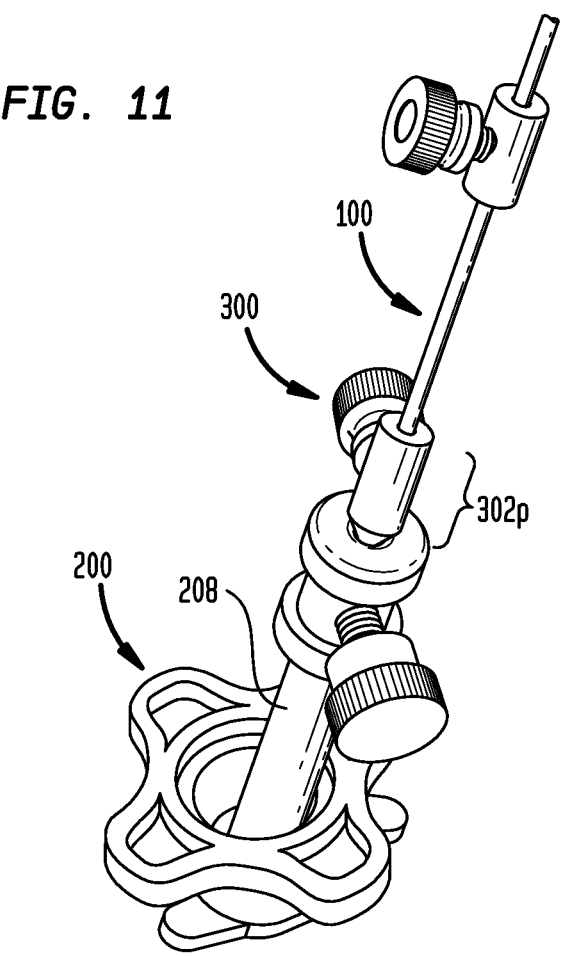
FIG. 11 is perspective view of the tip protector of FIG. 3, the microcatheter of FIG. 1, the depth stop of FIG. 10, and an exemplary stereotactic system.

As shown above and in FIG. 11, the tip protector 300 can be sized to be received within the inner lumen of the NAVIGUS system 200. For example, the distal portion 302d of the tip protector 300 can have a length that is equal to the length of the stem 208, such that when the tip protector is inserted up to the proximal, increased-diameter portion 302p, the distal end of the tip protector is aligned with the distal end or center of the pivoting stem, which typically serves as the depth reference point in the system 200. This can advantageously allow for simple depth registration between the catheter 100, the tip protector 300, and the system 200. In some embodiments, the distal portion 302d of the tip protector 300 has a length of approximately 5 cm.

Figure 12:
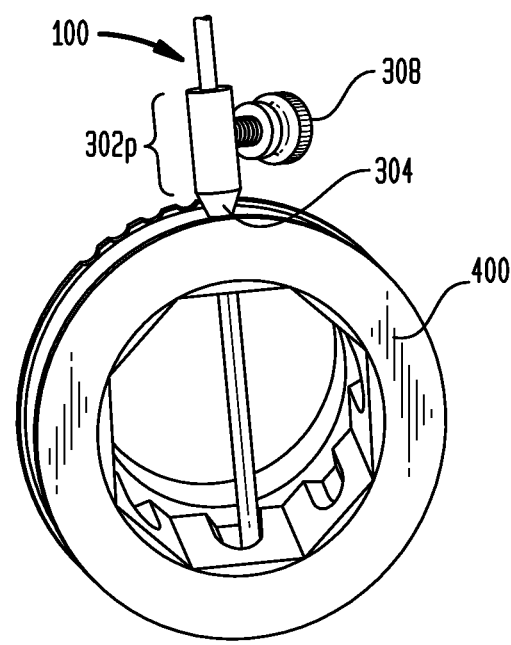
FIG. 12 is a perspective view of the tip protector of FIG. 3, the microcatheter of FIG. 1, and another exemplary stereotactic system.

Similarly, as shown in FIG. 12, the length of the tip protector 300 can be selected to correspond with the diameter of the circular guide block 400 of the VARIOGUIDE system, thereby facilitating depth registration between the catheter 100, the tip protector 300, and the system.

Figure 13:
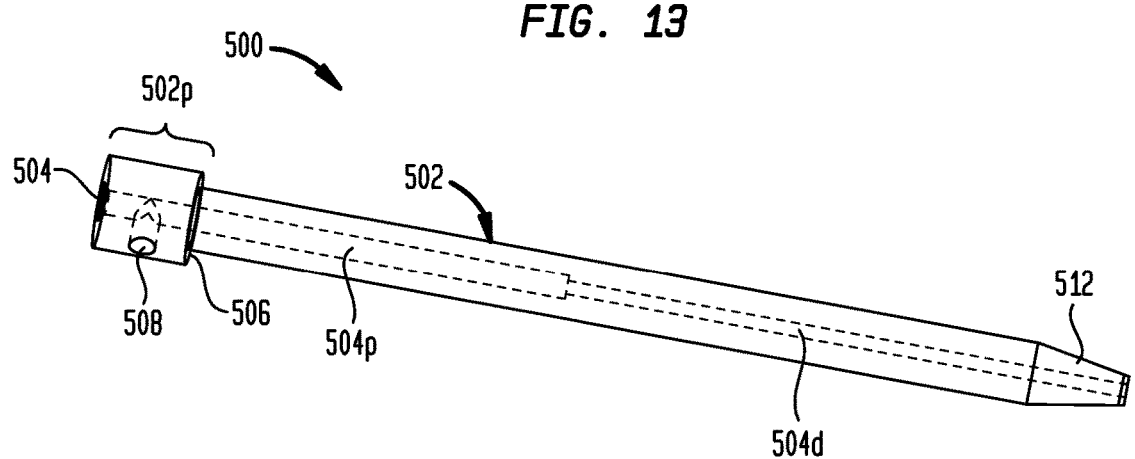
FIG. 13 is a perspective view of an exemplary guide tube.

In some embodiments, a guide tube can be provided to facilitate coupling of the tip protector 300 and/or the catheter 100 to the stereotactic system. FIG. 13 illustrates an exemplary embodiment of a guide tube 500. As shown, the guide tube 500 has an elongate body 502 with a central lumen 504 extending longitudinally therethrough. The inside diameter of the central lumen 504 is stepped, such that the lumen includes an increased-diameter proximal portion 504p sized to receive the distal end 302d of the tip protector 300 and a decreased-diameter distal portion 504d sized to snugly receive a portion of the catheter 100 that protrudes from the distal end of the tip protector. The guide tube 500 also has a proximal end 502p with an enlarged outside diameter such that a shoulder 506 is defined on the exterior of the guide tube. In use, the guide tube 500 can be inserted distally through the guide block of a stereotactic system until the shoulder 506 engages the guide block. The tip protector 300 can be inserted into the central lumen 504 of the guide tube 500 such that the tip protector is supported and stabilized in the stereotactic system. A lateral opening 508 can be included in the proximal end of the guide tube 500 to receive a set screw 510 for locking the tip protector 300 in place within the central lumen 504. The enlarged proximal end 502p of the guide tube 500 can have a standard length (e.g., 1 cm) to aid in depth registration. The guide tube 500 can also include a tapered distal tip 512 for easy insertion of the guide tube into the guide block of the stereotactic system.

Figure 14:
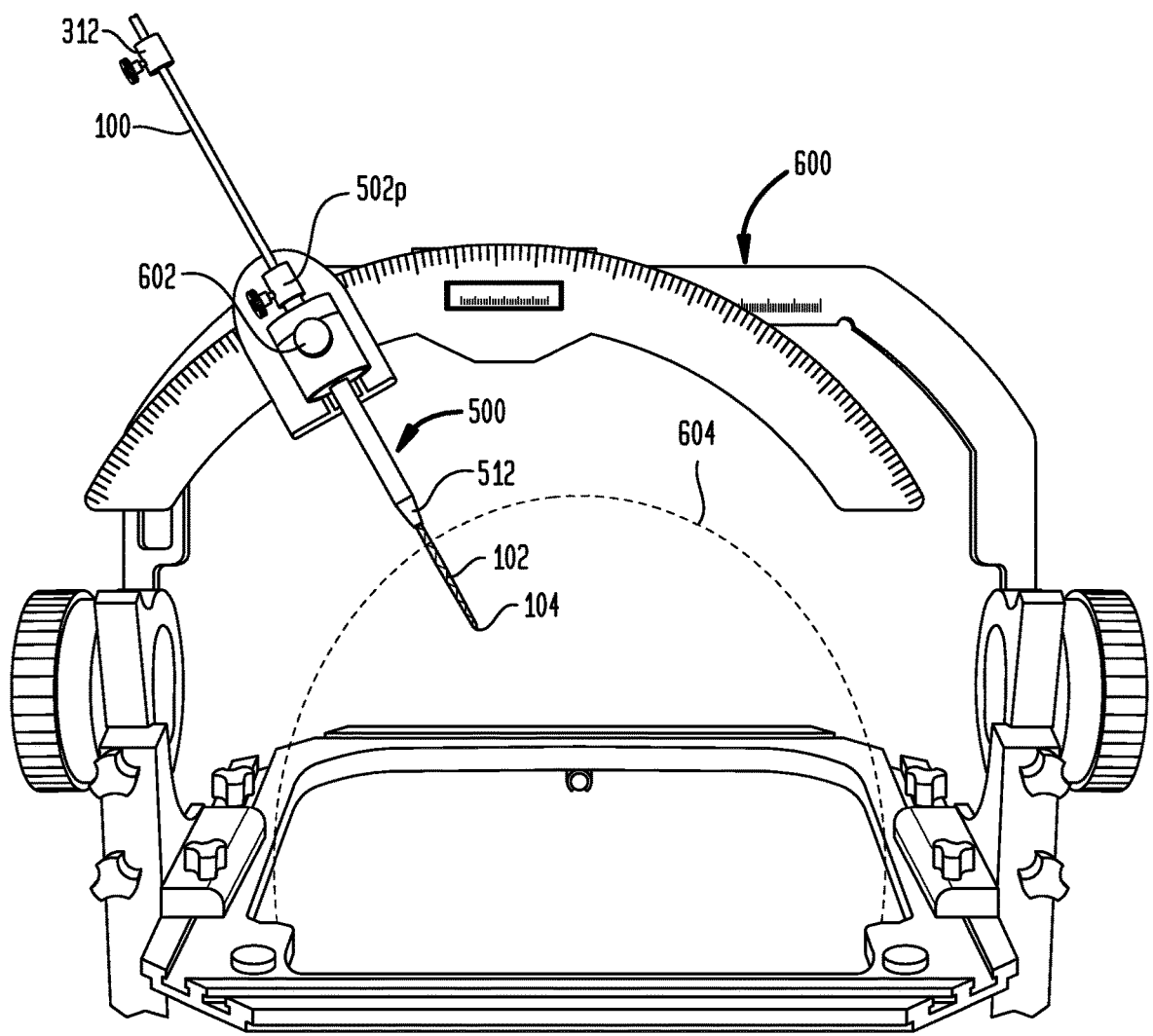
FIG. 14 is a perspective view of the tip protector of FIG. 3, the microcatheter of FIG. 1, the guide tube of FIG. 13, and another exemplary stereotactic system.

FIG. 14 illustrates an exemplary frame-based stereotactic system—the CRW frame available from INTEGRA LIFESCIENCES. As shown, the guide tube 500 can be sized to fit the existing guide block 602 of the frame 600 and help guide the catheter 100 from the guide block to the top of the skull 604. For example, the guide tube 500 can have an outside diameter of 0.25" to correspond with the inside diameter of the frame's guide block 602. The guide tube 500 can thus allow the frame 600 to be used with microcatheters 100 that would not otherwise fit in the guide block 602. In some embodiments, a kit including a plurality of guide tubes having different lengths can be provided. Accordingly, as the arc of the frame 600 is moved towards or away from the patient's skull 604 depending on target depth, a guide tube having an appropriate length can be selected such that the guide tube supports the full length or a significant portion of the full length of the microcatheter 100 extending between the guide block 602 and the skull 604.

FIG. 15 is a schematic illustration of a microcatheter 100 coupled to a tip protector 300 and depth stop 312 and aligned with the guide tube 500. FIG. 16 is a schematic illustration of the microcatheter 100 and tip protector 300 inserted through the guide tube 500. As shown, the tip protector 300 can be advanced until the enlarged proximal end 302p of the tip protector engages the proximal end surface of the guide tube 500.

Figure 17:
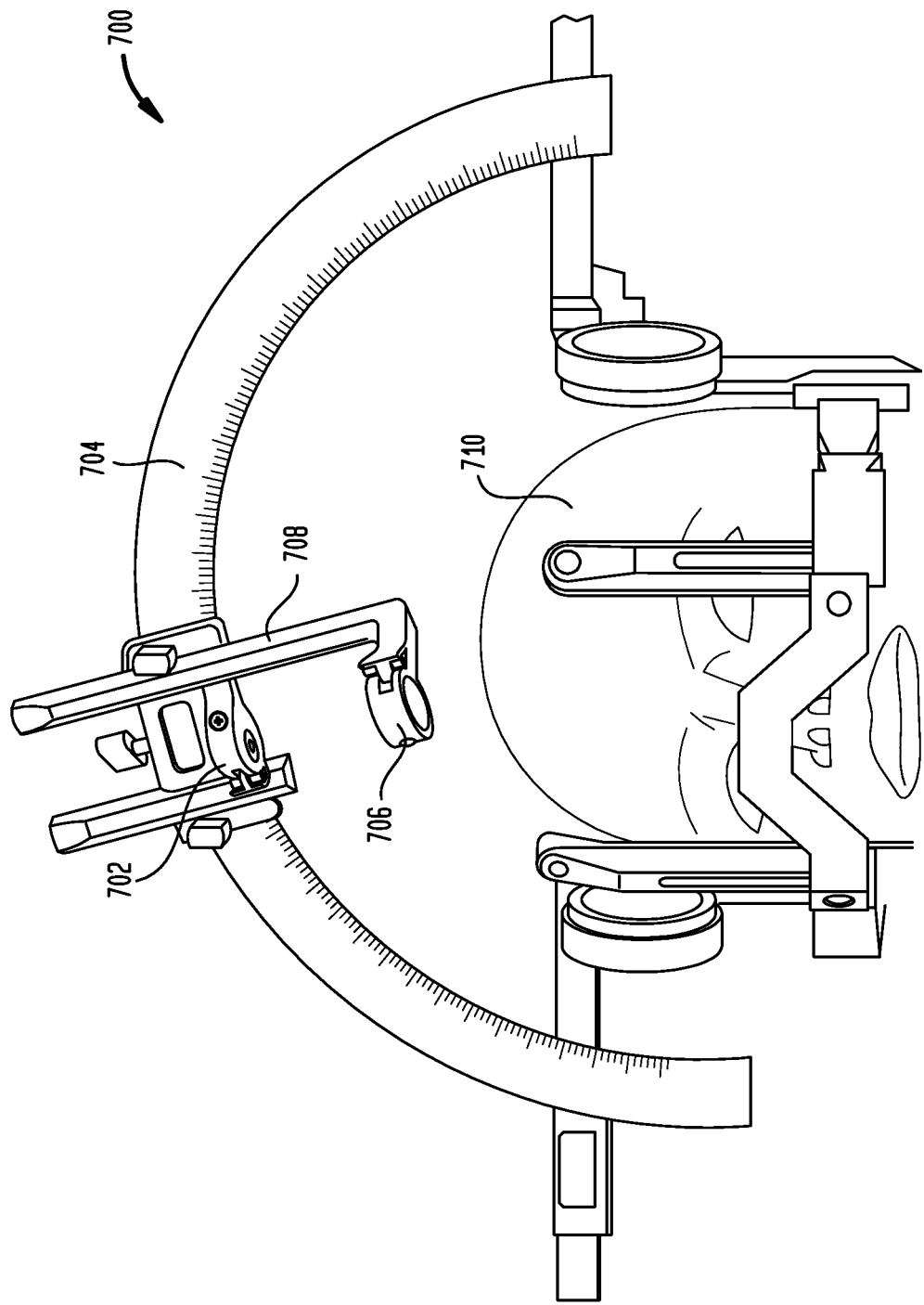
FIG. 17 is a perspective view of another exemplary stereotactic system.

FIG. 17 illustrates another exemplary frame-based stereotactic system—the LEKSELL frame available from ELEKTA. As shown, the system 700 includes an upper guide stop 702 mounted to the arc 704 of the frame. The system 700 also includes a lower guide block 706 mounted to an arm 708 that extends down from the arc 704 towards the patient's skull 710. In some embodiments, a guide stop adapter 802 and a guide block adapter 804 can be provided to facilitate coupling of the guide tube 500, tip protector 300, and/or the catheter 100 to the LEKSELL system 700 or to other similar systems.

Figure 18:
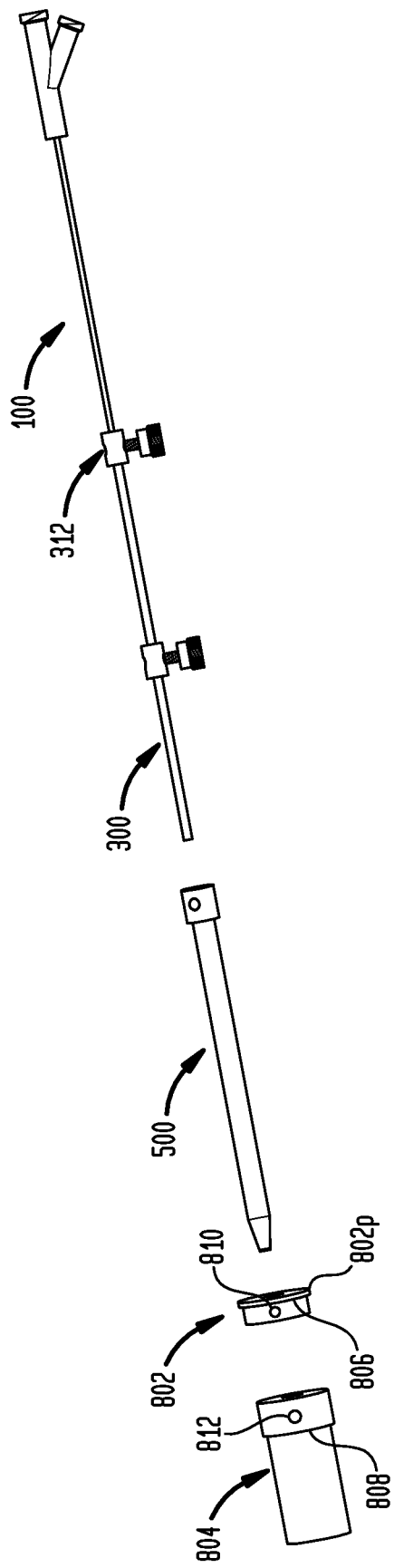
FIG. 18 is a perspective view of the tip protector of FIG. 3, the microcatheter of FIG. 1, the depth stop of FIG. 10, the guide tube of FIG. 13, an exemplary guide stop adapter, and an exemplary guide block adapter.
Figure 19:
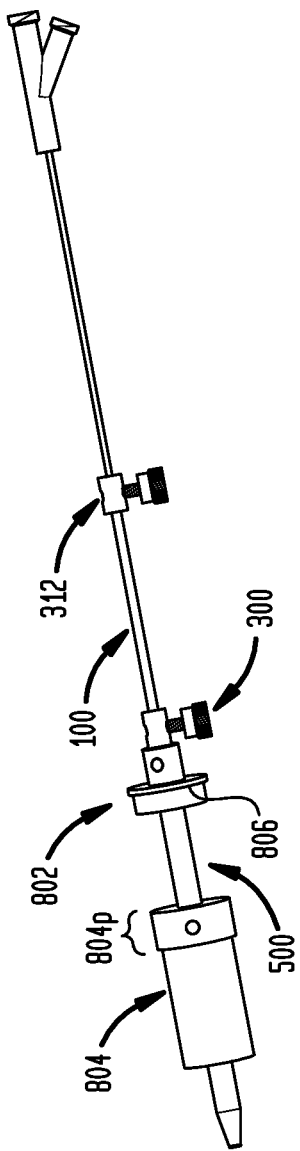
FIG. 19 is another perspective view of the tip protector of FIG. 3, the microcatheter of FIG. 1, the depth stop of FIG. 10, the guide tube of FIG. 13, and the guide stop and guide block adapters of FIG. 18.
Figure 20:
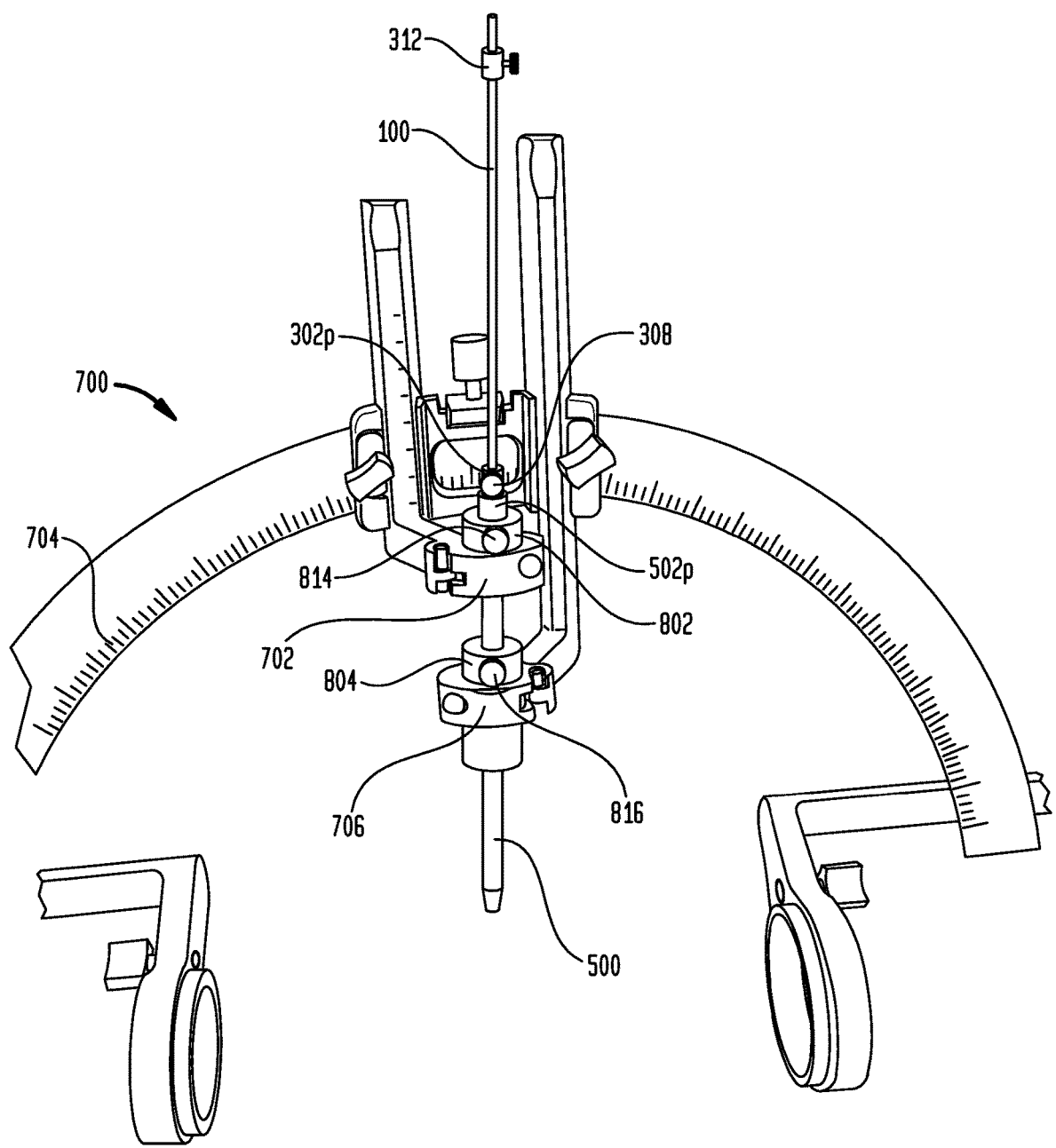
FIG. 20 is a perspective view of the tip protector of FIG. 3, the microcatheter of FIG. 1, the depth stop of FIG. 10, the guide tube of FIG. 13, the guide stop and guide block adapters of FIG. 18, and an exemplary stereotactic system.

FIG. 18 illustrates a microcatheter 100 (with a depth stop 312 and a tip protector 300), a guide tube 500, a guide stop adapter 802, and a guide block adapter 804. These components are illustrated in an assembled configuration in FIG. 19 and installed in the LEKSELL frame 700 in FIG. 20.

As shown, the guide stop adapter 802 can be a cylindrical disc having an inside diameter sized to receive the guide tube 500 and an outside diameter sized to fit within the guide stop 702 of the stereotactic system 700. The guide stop adapter 802 can include an enlarged proximal end 802p that defines an exterior shoulder 806.

The guide block adapter 804 can be a cylindrical sleeve having an inside diameter sized to receive the guide tube 500 and an outside diameter sized to fit within the guide block 706 of the stereotactic system 700. The guide block adapter 804 can include an enlarged proximal end 804p that defines an exterior shoulder 808. Lateral openings 810, 812 can be formed in the guide stop adapter 802 and/or the guide block adapter 804 to receive set screws 814, 816 for locking the guide tube 500 in position. In use, the guide stop adapter 802 and the guide block adapter 804 can be fitted to the guide stop 702 and guide block 706, respectively, of the stereotactic frame 700 and adjusted to the desired heights. The guide tube 500 can then be inserted through the adapters 802, 804, and can be secured in a fixed longitudinal position by tightening the set screws 814, 816 of the guide stop adapter 802 and the guide block adapter 804. The microcatheter 100 and attached tip protector 300 can then be inserted through the guide tube 500. The set screw of the guide tube 500 can be tightened to secure the tip protector 300 to the guide tube, before or after advancing the microcatheter 100 relative to the tip protector to the desired depth. The set screw 308 of the tip protector 300 can also be tightened to secure the microcatheter 100 in a fixed longitudinal position relative to the tip protector.

It will be appreciated that similar adapters can be made to fit other frames to facilitate stereotactic use of the tip protectors and microcatheters disclosed herein. The systems and methods disclosed herein can facilitate precision-targeted drug delivery (e.g., via convection-enhanced delivery) using a stereotactic system and a microcatheter. In an exemplary embodiment, a stereotactic system is registered to a patient, for example using MR images. A microcatheter and associated tip protector can be coupled to the stereotactic system using one or more guide tubes, guide block adapters, and/or guide stop adapters as disclosed herein and aimed towards a target site in the patient. The microcatheter can then be advanced into the patient under stereotactic guidance until one or more fluid outlet ports of the microcatheter are positioned at the target site. Drug-containing fluid can then be infused under positive pressure to deliver the drug through the catheter to the target site via convection-enhanced delivery.

The tip protectors, depth stops, fixtures, adapters, guides, and other components or devices disclosed herein can be manufactured or produced using any of a variety of techniques, including extrusion, molding, machining, and combinations thereof. The tip protectors, depth stops, fixtures, adapters, guides, and other components or devices disclosed herein can be formed from a variety of materials, including silastic, poly-urethane, poly-ester, PTFE, E-PTFE, stainless steel, titanium, polycarbonate, PVC, Delrin, aluminum, PEEK, plastic, metal, and combinations thereof.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A tip protection device, comprising:
   an elongate body having a central lumen extending longitudinally therethrough, the lumen being sized and configured to slidably receive a catheter; and
   a locking mechanism configured to selectively maintain the elongate body in a fixed longitudinal position relative to a catheter inserted through the central lumen;
   wherein the distal tip is separable from the elongate body along a perforated snap portion.

2. The device of claim 1, wherein the locking mechanism comprises a screw.

3. The device of claim 1, wherein the elongate body includes an increased-diameter portion configured to act as a depth stop when the elongate body is inserted through a lumen of a stereotactic system.

4. The device of claim 1, wherein the elongate body is formed from at least one of silastic, poly-urethane, poly-ester, PTFE, E-PTFE, stainless steel, polycarbonate, PVC, Delrin, aluminum, PEEK, plastic, metal, and titanium.

5. The device of claim 1, wherein the elongate body is fabricated using at least one of extrusion, molding, and machining.

6. The device of claim 1, wherein the elongate body comprises a sharpened distal tip.

7. The device of claim 1, wherein the elongate body comprises a distal cylindrical portion having a first diameter and a proximal cylindrical portion having a second diameter that is greater than the first diameter.

8. The device of claim 1, wherein the central lumen has a diameter of about 0.5 mm to about 4.0 mm.

9. A system comprising:
   the tip protection device of claim 1; and
   a depth stop comprising a cylindrical body portion having a central lumen extending longitudinally therethrough and a second locking mechanism configured to selectively engage a catheter inserted through the cylindrical body portion.

10. A system comprising:
    the tip protection device of claim 1; and
    a guide tube comprising:
      an elongate body having a central lumen extending longitudinally therethrough, the central lumen including a proximal portion having a first diameter and a distal portion having a second diameter that is less than the first diameter, the proximal portion being sized to receive a reduced diameter distal portion of the tip protection device and the distal portion being sized to receive at least a portion of a catheter inserted through the tip protection device.

11. The system of claim 10, wherein the elongate body of the guide tube includes a proximal portion having an outside diameter which is greater than an outside diameter of a distal portion of the elongate body of the guide tube.

12. The system of claim 10, wherein a distal end of the guide tube is tapered.

13. The system of claim 10, further comprising:
a guide stop adapter comprising a cylindrical disc having an inside diameter sized to receive the distal portion of the guide tube therethrough and an outside diameter sized to fit within a guide stop of a stereotactic system; and
a guide block adapter comprising a cylindrical sleeve having an inside diameter sized to receive the distal portion of the guide tube therethrough and an outside diameter sized to fit within a guide block of a stereotactic system;
wherein the guide tube has a length sufficient to span a distance between the guide block
of the stereotactic system and a skull of a patient to which the stereotactic system is registered.

14. A system, comprising:
a tip protection device, comprising:
an elongate body having a central lumen extending longitudinally therethrough, the lumen being sized and configured to slidably receive a catheter; and
a locking mechanism configured to selectively maintain the elongate body in a fixed longitudinal position relative to a catheter inserted through the central lumen; and
a guide tube comprising:
an elongate body having a central lumen extending longitudinally therethrough, the central lumen including a proximal portion having a first diameter and a distal portion having a second diameter that is less than the first diameter, the proximal portion being sized to receive a reduced diameter distal portion of the tip protection device and the distal portion being sized to receive at least a portion of a catheter inserted through the tip protection device; and
a set screw received in a lateral opening formed in a proximal end of the guide tube, the set screw locking the tip protection device in place within the central lumen of the elongate body of the guide tube.

15. The system of claim 14, wherein the locking mechanism comprises a screw.

16. The system of claim 14, wherein the elongate body of the tip protection device includes an increased-diameter portion configured to act as a depth stop when the elongate body of the tip protection device is inserted through a lumen of a stereotactic system.

17. The system of claim 14, wherein the elongate body of the tip protection device is formed from at least one of silastic, PTFE, Delrin, PEEK, plastic, and metal.

18. The system of claim 17, wherein the PTFE15E-PTFE.

19. The system of claim 17, wherein the plastic comprises at least one of polyurethane, polycarbonate, polyester, and PVC.

20. The system of claim 17, wherein the metal comprises at least one of titanium, aluminum, and stainless steel.

21. The system of claim 14, wherein the elongate body of the tip protection device is fabricated using at least one of extrusion, molding, and machining.

22. The system of claim 14, wherein the elongate body of the tip protection device comprises a sharpened distal tip.

23. The system of claim 22, wherein the distal tip is separable from the elongate body of the tip protection device along a perforated snap portion.

24. The system of claim 14, wherein the elongate body of the tip protection device comprises a distal cylindrical portion having a first diameter and a proximal cylindrical portion having a second diameter that is greater than the first diameter.

25. The system of claim 14, wherein the central lumen of the tip protection device has a diameter of 0.5 mm to 4.0 mm.

26. The system of claim 14, further comprising a depth stop comprising a cylindrical body portion having a central lumen extending longitudinally therethrough and a second locking mechanism configured to selectively engage a catheter inserted through the cylindrical body portion.

27. The system of claim 14, wherein the elongate body of the guide tube includes a proximal portion having an outside diameter which is greater than an outside diameter of a distal portion of the elongate body of the guide tube.

28. The system of claim 14, wherein a distal end of the guide tube is tapered.

29. The system of claim 14, further comprising:
a guide stop adapter comprising a cylindrical disc having an inside diameter sized to receive the distal portion of the guide tube therethrough and an outside diameter sized to fit within a guide stop of a stereotactic system; and
a guide block adapter comprising a cylindrical sleeve having an inside diameter sized to receive the distal portion of the guide tube therethrough and an outside diameter sized to fit within a guide block of a stereotactic system;
wherein the guide tube has a length sufficient to span a distance between the guide block
of the stereotactic system and a skull of a patient to which the stereotactic system is registered.

30. A system, comprising:
a tip protection device, comprising:
an elongate body having a central lumen extending longitudinally therethrough, the lumen being sized and configured to slidably receive a catheter; and
a locking mechanism configured to selectively maintain the elongate body in a fixed longitudinal position relative to a catheter inserted through the central lumen; and
a guide tube comprising an elongate body having a central lumen extending longitudinally therethrough;
the elongate body of the tip protection device including a portion configured to act as a depth stop when the elongate body of the tip protection device is inserted through the central lumen of the guide tube;
a set screw received in a lateral opening formed in a proximal end of the guide tube, the set screw locking the tip protection device in place within the central lumen of the elongate body of the guide tube;
a guide stop adapter comprising a cylindrical disc having an inside diameter sized to receive the distal portion of the guide tube therethrough and an outside diameter sized to fit within a guide stop of a stereotactic system; and
a guide block adapter comprising a cylindrical sleeve having an inside diameter sized to receive the distal portion of the guide tube therethrough and an outside diameter sized to fit within a guide block of a stereotactic system;
wherein the guide tube has a length sufficient to span a distance between the guide block of the stereotactic system and a skull of a patient to which the stereotactic system is registered.

31. The system of claim 30, wherein the locking mechanism comprises a screw.

32. The system of claim 30, wherein the elongate body of the tip protection device is formed from at least one of silastic, PTFE, Delrin, PEEK, plastic, and metal.

33. The system of claim 32, wherein the PTFE is E-PTFE.

34. The system of claim 32, wherein the plastic comprises at least one of polyurethane, polycarbonate, polyester, and PVC.

35. The system of claim 32, wherein the metal comprises at least one of titanium, aluminum, and stainless steel.

36. The system of claim 30, wherein the elongate body of the tip protection device is fabricated using at least one of extrusion, molding, and machining.

37. The system of claim 30, wherein the elongate body of the tip protection device comprises a sharpened distal tip.

38. The system of claim 37, wherein the distal tip is separable from the elongate body of the tip protection device along a perforated snap portion.

39. The system of claim 30, wherein the elongate body of the tip protection device comprises a distal cylindrical portion having a first diameter and a proximal cylindrical portion having a second diameter that is greater than the first diameter.

40. The system of claim 30, wherein the central lumen of the tip protection device has a diameter of 0.5 mm to 4.0 mm.

41. The system of claim 30, further comprising a depth stop comprising a cylindrical body portion having a central lumen extending longitudinally therethrough and a second locking mechanism configured to selectively engage a catheter inserted through the cylindrical body portion.

42. The system of claim 30, wherein the elongate body of the guide tube includes a proximal portion having an outside diameter which is greater than an outside diameter of a distal portion of the elongate body of the guide tube.

43. The system of claim 30, wherein a distal end of the guide tube is tapered.

* * * * *